United States Patent
Heindl et al.

(10) Patent No.: US 11,423,541 B2
(45) Date of Patent: Aug. 23, 2022

(54) ASSESSMENT OF DENSITY IN MAMMOGRAPHY

(71) Applicant: KHEIRON MEDICAL TECHNOLOGIES LTD, London (GB)

(72) Inventors: Andreas Heindl, London (GB); Galvin Khara, London (GB); Joseph Yearsley, London (GB); Michael O'Neill, London (GB); Peter Kecskemethy, London (GB); Tobias Rijken, London (GB); Edith Karpati, Budapest (HU)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 0 days.

(21) Appl. No.: 16/604,662

(22) PCT Filed: Apr. 12, 2018

(86) PCT No.: PCT/GB2018/050979
§ 371 (c)(1),
(2) Date: Oct. 11, 2019

(87) PCT Pub. No.: WO2018/189549
PCT Pub. Date: Oct. 18, 2018

(65) Prior Publication Data
US 2020/0074632 A1 Mar. 5, 2020

(30) Foreign Application Priority Data

Apr. 12, 2017 (GB) .................................. 1705911
Jul. 18, 2017 (GB) .................................. 1711557

(51) Int. Cl.
*A61B 5/00* (2006.01)
*A61B 5/055* (2006.01)
(Continued)

(52) U.S. Cl.
CPC ............ *G06T 7/0014* (2013.01); *A61B 5/055* (2013.01); *A61B 5/4312* (2013.01);
(Continued)

(58) Field of Classification Search
None
See application file for complete search history.

(56) References Cited

U.S. PATENT DOCUMENTS 5,768,406 A 6/1998 Abdel-Mottaleb
5,999,639 A 12/1999 Rogers et al.
(Continued)

FOREIGN PATENT DOCUMENTS

CN 105931226 A 9/2016
CN 106096491 A 11/2016
(Continued)

OTHER PUBLICATIONS

Menechelli et al. "Automatic breast tissue density estimation scheme in digital mammography images," Proc. SPIE 10136, Medical Imaging 2017: Image Perception, Observer Performance, and Technology Assessment, 101361J (Mar. 10, 2017); doi: 10.1117/12.2253186 (Year: 2017).*

(Continued)

*Primary Examiner* — Soo Shin
(74) *Attorney, Agent, or Firm* — Finch & Maloney PLLC

(57) ABSTRACT

The present invention relates to a method and system that automatically classifies tissue type/patterns and density categories in mammograms. More particularly, the present invention relates to improving the quality of assessing density and tissue pattern distribution in mammography.
According to a first aspect, there is provided a computer-aided method of analysing mammographic images, the method comprising the steps of: receiving a mammogram; segmenting one or more anatomical regions of the mammo-
(Continued)

gram; identifying a tissue type and a density category classification for an anatomical region; and using the identified tissue type and density category classifications to generate classifications output for the mammogram.

20 Claims, 4 Drawing Sheets

(51) Int. Cl.
*A61B 6/00* (2006.01)
*A61B 6/03* (2006.01)
*G06N 3/08* (2006.01)
*G06T 7/00* (2017.01)
*G06T 7/11* (2017.01)
*G06T 7/136* (2017.01)
*G06T 7/143* (2017.01)
*G06T 7/33* (2017.01)
*G06T 7/77* (2017.01)
*G16H 30/20* (2018.01)
*G16H 30/40* (2018.01)
*G16H 50/20* (2018.01)
*G16H 50/30* (2018.01)

(52) U.S. Cl.
CPC .......... *A61B 5/7264* (2013.01); *A61B 5/7267* (2013.01); *A61B 5/7282* (2013.01); *A61B 6/032* (2013.01); *A61B 6/502* (2013.01); *A61B 6/5217* (2013.01); *G06N 3/08* (2013.01); *G06T 7/0012* (2013.01); *G06T 7/0016* (2013.01); *G06T 7/11* (2017.01); *G06T 7/136* (2017.01); *G06T 7/143* (2017.01); *G06T 7/337* (2017.01); *G16H 30/20* (2018.01); *G16H 30/40* (2018.01); *G16H 50/20* (2018.01); *G16H 50/30* (2018.01); *G06T 2207/10081* (2013.01); *G06T 2207/10088* (2013.01); *G06T 2207/10116* (2013.01); *G06T 2207/20081* (2013.01); *G06T 2207/20084* (2013.01); *G06T 2207/30068* (2013.01); *G06T 2207/30096* (2013.01)

(56) References Cited

U.S. PATENT DOCUMENTS

| | | | |
|---|---|---|---|
| 6,058,322 A | 5/2000 | Nishikawa et al. | |
| 6,075,879 A | 6/2000 | Roehrig et al. | |
| 6,324,532 B1 | 11/2001 | Spence et al. | |
| 6,463,425 B2 | 10/2002 | Raz | |
| 6,574,304 B1 | 6/2003 | Hsieh et al. | |
| 7,490,085 B2 | 2/2009 | Walker et al. | |
| 9,589,374 B1* | 3/2017 | Gao | G06T 11/008 |
| 10,127,659 B2 | 11/2018 | Hsieh et al. | |
| 10,223,610 B1 | 3/2019 | Akselrod-Ballin et al. | |
| 11,127,137 B2 | 9/2021 | Heindl et al. | |
| 2004/0184644 A1 | 9/2004 | Leichter et al. | |
| 2004/0228509 A1 | 11/2004 | Holupka et al. | |
| 2005/0010445 A1 | 1/2005 | Krishnan et al. | |
| 2005/0049497 A1 | 3/2005 | Krishnan et al. | |
| 2005/0113651 A1 | 5/2005 | Wood et al. | |
| 2006/0050958 A1 | 3/2006 | Okada et al. | |
| 2006/0100507 A1 | 5/2006 | Mertelmeier | |
| 2006/0122467 A1 | 6/2006 | Harrington et al. | |
| 2006/0177125 A1 | 8/2006 | Chan et al. | |
| 2006/0274928 A1 | 12/2006 | Collins et al. | |
| 2007/0003119 A1 | 1/2007 | Roehrig et al. | |
| 2007/0183641 A1 | 8/2007 | Peters et al. | |
| 2008/0159613 A1 | 7/2008 | Luo et al. | |
| 2009/0041327 A1 | 2/2009 | Chen et al. | |
| 2009/0118640 A1 | 5/2009 | Miller et al. | |
| 2009/0274349 A1 | 11/2009 | Cascio et al. | |
| 2010/0135562 A1 | 6/2010 | Greenberg et al. | |
| 2010/0256459 A1 | 10/2010 | Miyasa et al. | |
| 2010/0256991 A1 | 10/2010 | Ishikawa et al. | |
| 2011/0123087 A1 | 5/2011 | Nie et al. | |
| 2011/0150313 A1 | 6/2011 | Su et al. | |
| 2012/0099771 A1 | 4/2012 | Lao | |
| 2013/0218045 A1 | 8/2013 | Ironstone | |
| 2013/0236078 A1 | 9/2013 | Kobayashi et al. | |
| 2013/0322711 A1 | 12/2013 | Schultz et al. | |
| 2013/0343626 A1 | 12/2013 | Rico et al. | |
| 2014/0001681 A1 | 1/2014 | Hargett et al. | |
| 2014/0018681 A1 | 1/2014 | Chang et al. | |
| 2014/0355840 A1* | 12/2014 | Pearson Peyton | G06T 7/0014 |
| | | | 382/115 |
| 2016/0314579 A1 | 10/2016 | Ghouti et al. | |
| 2016/0350946 A1 | 12/2016 | Schieke et al. | |
| 2016/0361121 A1 | 12/2016 | Reicher et al. | |
| 2016/0364528 A1 | 12/2016 | Reicher et al. | |
| 2016/0364857 A1 | 12/2016 | Reicher et al. | |
| 2017/0039412 A1 | 2/2017 | Solanki et al. | |
| 2017/0200266 A1 | 7/2017 | Podilchuk et al. | |
| 2018/0033144 A1 | 2/2018 | Risman et al. | |
| 2018/0061054 A1 | 3/2018 | Abraham et al. | |
| 2018/0129900 A1 | 5/2018 | Kiraly et al. | |
| 2018/0165809 A1* | 6/2018 | Stanitsas | G06T 7/0012 |
| 2018/0218495 A1 | 8/2018 | Ben-Ari | |
| 2018/0218497 A1 | 8/2018 | Golden et al. | |
| 2019/0189263 A1 | 6/2019 | Stoval, III et al. | |
| 2019/0340763 A1 | 11/2019 | Laserson | |
| 2020/0074632 A1* | 3/2020 | Heindl | A61B 6/502 |
| 2020/0074634 A1 | 3/2020 | Kecskemethy et al. | |
| 2020/0167928 A1 | 5/2020 | Heindl et al. | |
| 2020/0342589 A1 | 10/2020 | Heindl et al. | |
| 2021/0035296 A1 | 2/2021 | Mahrooghy et al. | |
| 2021/0248744 A1 | 8/2021 | Rijken et al. | |
| 2021/0312618 A1 | 10/2021 | Kecskemethy et al. | |
| 2021/0313043 A1 | 10/2021 | Kecskemethy et al. | |

FOREIGN PATENT DOCUMENTS

| | | |
|---|---|---|
| CN | 106204587 A | 12/2016 |
| EP | 3806744 A1 | 4/2021 |
| GB | 2579244 A | 6/2020 |
| JP | 2006255412 A | 9/2006 |
| JP | 2008541889 A | 11/2008 |
| JP | 2013039230 A | 2/2013 |
| JP | 2016534709 A | 11/2016 |
| WO | 9905503 | 2/1999 |
| WO | 2005001740 A2 | 1/2005 |
| WO | 2005001742 A2 | 1/2005 |
| WO | 2008050332 A2 | 5/2008 |
| WO | 2008088478 A1 | 7/2008 |
| WO | 2015031641 A1 | 3/2015 |
| WO | 2015077076 A1 | 5/2015 |
| WO | 2016057960 A1 | 4/2016 |
| WO | 2017210690 A1 | 12/2017 |
| WO | 2018189541 A1 | 10/2018 |
| WO | 2018189549 A1 | 10/2018 |
| WO | 2018189550 A1 | 10/2018 |
| WO | 2018189551 A1 | 10/2018 |
| WO | 2019239153 A1 | 12/2019 |

OTHER PUBLICATIONS

Gram et al., "The Tabar classification of mammographic parenchymal patterns," European Journal of Radiology 24 (1997) 131-136 (Year: 1997).*

Akselrod-Ballin et al., "A Region Based Convolution Network for Tumor Detection and Classification in Breast Mammography," In: Carneiro G. et al. (eds) Deep Learning and Data Labeling for Medical Applications. DLMIA 2016, LABELS 2016. Lecture Notes in Computer Science, vol. 10008. (Year: 2016).*

Sun et al., "Enhancing deep convolutional neural network scheme for breast cancer diagnosis with unlabeled data," Computerized Medical Imaging and Graphics 57 (2017) 4-9. Available online Jul. 19, 2016. (Year: 2016).*

(56) References Cited

OTHER PUBLICATIONS

Winkel et al., "Mammogreaphic density and structural features can individually and jointly contribute to breast cancer risk assessment in mammography screening: a case-control study," BMC Cancer (2016) 16:414 (Year: 2016).*

International Search Report and Written Opinion received for Patent Application No. PCT/GB2018/050969, dated Jun. 26, 2018. 20 pages.

International Preliminary Report on Patentability received for Patent Application No. PCT/GB2018/050969, dated Oct. 15, 2019. 12 pages.

International Search Report and Written Opinion received for PCT Application No. PCT/GB2018/050980, dated Jul. 12, 2018. 34 pages.

International Preliminary Report on Patentability received for PCT Application No. PCT/GB2018/050980, dated Oct. 15, 2019. 11 pages.

Combined Search and Examination Report under Sections 17 and 18(3) received for GB Application No. 1711558.5, dated Dec. 22, 2017. 6 pages.

International Search Report and Written Opinion received for Patent Application No. PCT/GB2018/050979, dated Jul. 9, 2018. 36 pages.

International Preliminary Report on Patentability received for Patent Application No. PCT/GB2018/050979, dated Oct. 15, 2019. 11 pages.

Combined Search and Examination Report under Sections 17 and 18(3) received for GB Application No. 1711557.7, dated Jan. 18, 2018. 5 pages.

International Search Report and Written Opinion received for Patent Application No. PCT/GB2018/050981, dated Jul. 9, 2018. 23 pages.

International Preliminary Report on Patentability received for Patent Application No. PCT/GB2018/050981, dated Oct. 15, 2019. 15 pages.

Combined Search and Examination Report under Sections 17 and 18(3) received for GB Application No. 1711559.3 dated Dec. 19, 2017. 7 pages.

Christ, et al., "Automatic Liver and Tumor Segmentation of CT and MRI Volumes Using Cascaded Fully Convolutional Neural Networks," arXiv: 1702.05970v2 [cs.CV], Feb. 23, 2017. 20 pages.

Christ, et al., "Survivalnet: Predicting Patient Survival From Diffusion Weighted Magnetic Resonance Images Using Cascaded Fully Convolutional and 3D Convolutional Neural Networks," arXiv: 1702.05941v1 [cs.CV], Feb. 20, 2017. 6 pages.

Hou, et al., "Patch-based Convolutional Neural Network for Whole Slide Tissue Image Classification," IEEE Conference on Computer Vision and Pattern Recognition, (CVPR) Jun. 27, 2016. pp. 2424-2433.

Menechelli, et al., "Automatic breast tissue density estimation scheme in digital mammography images," Progress in Biomedical Optics and Imaging, SPIE—International Society for Optical Engineering., vol. 10136, Mar. 10, 2017. 12 pages.

Ronneberger, et al., "U-Net: Convolutional Networks for Biomedical Image Segmentation," Medical Image Computing and Computer-Assisted Intervention—MICCAI 2015—18th International Conference. Nov. 18, 2015, Springer International Publishing, arXiv:1505.04597v1, May 18, 2015. 8 pages.

Yu, et al., "Automated Melanoma Recognition in Dermoscopy Images via Very Deep Residual Networks," IEEE Transactions on Medical Imaging. Dec. 2016. 12 pages.

El Hamdi, et al., "Breast Cancer Diagnosis Using a Hybrid Evolutionary Neural Network Classifier," 18th Mediterranean Conference on Control & Automation, Jun. 23-25, 2010, pp. 1308-1315.

Kallenberg, et al., "Unsupervised Deep Learning Applied to Breast Density Segmentation and Mammographic Risk Scoring," IEEE Transactions on Medical Imaging, vol. 35, No. 5, May 2016. pp. 1322-1331.

Winkel, et al., "Mammographic density and structural features can individually and jointly contribute to breast cancer risk assessment in mammography screening: a case-control study," BMC Cancer (2016) DOI 10.1186/s 12885-016-2450-7. pp. 1-12.

Communication pursuant to Article 94(3) EPC received for EP Application No. 18719271.1, dated Jun. 21, 2021. 10 pages.

Communication pursuant to Article 94(3) EPC received for EP Application No. 18719272.9, dated Jun. 21, 2021. 8 pages.

International Search Report and Written Opinion received for PCT/GB2019/051666, dated Oct. 2, 2019. 8 pages.

International Preliminary Report on Patentability received for PCT/GB2019/051666. Date of Report Completion, dated Oct. 7, 2020. 21 pages.

Canadian Office Action recieved for CN Application No. 3,102,170, dated Jan. 11, 2022. 5 pages.

GB Search Report under Section 17(5) received for GB Application No. GB1809796.4, dated Dec. 17, 2018. 4 pages.

GB Search Report under Section 17(5) received for GB Application No. GB1819329.2, dated May 28, 2019. 3 pages.

EP Communication under Rule 71(3) EPC issued for EP Application No. EP19744779.0, dated Sep. 29, 2021. 7 pages.

EP Communication under Rule 71(3) EPC issued for EP Application No. EP19744777.4, dated Sep. 30, 2021. 28 pages.

EP Communication under Rule 71(3) EPC issued for EP Application No. EP19744778.2 dated Sep. 7, 2021. 30 pages.

He, et al., "Mask R-CNN," 2017 IEEE International Conference on Computer Vision. Retrieved from the Internet on Oct. 8, 2021 from IEEE Xplore. pp. 2980-2988.

Jaeger, et al., "Retina U-Net Embarrassingly Simple Exploitation of Segmentation Supervision for Medical Object Detection," Proceedings of Machine Learning Research, arXiv: 1811, 08661v1 [cs.CV] Nov. 21, 2018. 10 pages.

Canadian Patent Application No. 3,102,170, (PCT/GB2019/051666); Requisition by Examination, dated Jul. 27. 2021, 5 pages.

Canadian Patent Application No. 3,102,174, (PCT/GB2019/051668); Requisition by Examination, dated Jul. 6, 2021, 4 pages.

Huo, et al., "Computerized Analysis of Multiple-Mammographic Views: Potential Usefulness of Special View Mammograms in Computer-Aided Diagnosis," IEEE Transactions on Medical Imaging, vol. 20., No. 12. Dec. 2001. pp. 1285-1292.

International Preliminary Report on Patentability received for PCT/GB2019/051667, dated Nov. 5, 2020. 20 pages.

International Preliminary Report on Patentability received for PCT/GB2019/051668, dated Oct. 5, 2020. 21 pages.

International Search Report and Written Opinion received for PCT/GB2019/051667, dated Nov. 12, 2019. 10 pages.

International Search Report and Written Opinion received for PCT/GB2019/051668, dated Nov. 15, 2019. 11 pages.

Kisilev, et al., "Medical Image Description Using Multi-task-loss CNN," Springer International Publishing AG, 2016. pp. 121-129.

Ribli, et al., "Detecting and classifying lesions in mammograms with Deep Learning," Scientific Reports, article No. 4165, published Mar. 15, 2018. 8 pages.

Zheng, et al., "Breast Cancer Screening Using Convolutional Neural Network and Follow-up Digital mammography," SPIE vol. 10669, 2018. 13 pages.

Akselrod-Ballin, et al., "A Region Based Convolutional Network for Tumor Detection and Classification in Breast Mammography,"Springer International Publishing AG, 2016. pp. 197-205.

Gram, et al., "The Tabar classification of mammographic parenchymal patterns," European Journal of Radiology 24 (1997) pp. 131-136.

Sun, et al., "Enhancing deep convolutional neural network scheme for breast cancer diagnosis with unlabeled data, 2016. URL: "https://www.elsevier.com/about/policies/open-access-licenses/elsevier-user-license. 21 pages.

Canadian Patent Application No. 3,102,173, (PCT/GB2019/051667); Requisition by Examination, dated Dec. 9, 2021. 6 pages.

Canadian Patent Application No. 3,102,173, (PCT/GB2019/051667); Requisition by Examination, dated Jun. 29, 2021, 6 pages.

Long, et al., "Fully Convolutional Networks for Semantic Segmentation," Proc. of IEEE Computer Vision and Pattern Recognition, 201, 3431-3440, https://openaccess.thecvf.com/content_cvpr_2015/papers/Long_Fully_Convolutional_Networks_2015_CVPR_paper.pdf.

(56) References Cited

OTHER PUBLICATIONS

JP Office Action issued for JP2020-505539, dated Mar. 8, 2022, 5 pages. (including English translation).
JP Office Action received for JP Application No. 2020-505540, dated Apr. 19, 2022. 3 pages.
He, "A Review on Automatic Mammographic Density and Parenchymal Segmentation," International Journal of Breast Cancer, vol. 2015, Article ID 276217, (2015). 31 pages.

\* cited by examiner

ASSESSMENT OF DENSITY IN MAMMOGRAPHY

FIELD

The present invention relates to a method and system that automatically classifies tissue type/patterns and density categories in mammograms. More particularly, the present invention relates to improving the quality of assessing density and tissue pattern distribution in mammography.

BACKGROUND

Mammography is a medical imaging modality widely used for breast cancer detection. Mammography makes use of "soft" X-rays to produce detailed images of the internal structure of the human breast. These images are called mammograms and this method is considered to be the gold standard in early detection of breast abnormalities which provide a valid diagnosis of a cancer in a curable phase.

Unfortunately, the procedure of analysing mammograms is often challenging. The density and tissue type of the breasts are highly varied and in turn present a high variety of visual features due to patient genetics. These background visual patterns can obscure the often-tiny signs of malignancies which may then be easily overlooked by the human eye. Thus, the analyses of mammograms often lead to false-positive or false-negative diagnostic results which may cause missed treatment (in the case of false-negatives) as well as unwanted psychological and sub-optimal downstream diagnostic and treatment consequences (in the case of false-positives).

Most developed countries maintain a population-wide screening program, a comprehensive system for calling in women of a certain age group, free of symptoms to have regular breast screening. These screening programs require highly standardized protocols to be followed by experienced specialist trained doctors who can reliably analyse a large number of mammograms routinely. Most professional guidelines strongly suggest reading of each mammogram by two equally expert radiologists (industrially known as double-reading). Nowadays, with the number of available highly skilled radiologists scarce and decreasing, the double-reading requirement is often impractical or impossible.

When analysing mammograms, the reliable identification of anatomical structures is important for visual evaluation and especially for analytic assessment of visual features based on their anatomic location and their relation to anatomic structures, which may have profound implications on the final diagnostic results. In the case that anatomic structures appear distorted, they may also indicate the presence of possible malignancies.

The analysis of mammograms is further complicated by visual confounding, obstructing, and/or occluding factors such as breast density or the type of structural pattern of the breast tissue. Both breast density and breast tissue type contributes to producing mammograms that are difficult to screen for cancer.

Uniformity of classification, by having a method of descriptively assigning objects into a predefined set of categories, reduces vague communication amongst professionals and ensures improved monitoring of breast cancer in mammography.

There are different types of patterns in breast tissue that affect the detectability of breast cancers. Thus, it is important for quality control reasons to know what kind of pattern is present. There are five mammography parenchymal patterns known as "Tabar patterns", named after professor Laszlo Tabar who developed this classification.

The Tabar patterns (or classifications) are based on a histologic-mammographic correlation with a three-dimensional, subgross (thick-slice) technique, and on the relative proportion of four "building blocks" (nodular densities, linear densities, homogeneous fibrous tissue, radiolucent fat tissue). The five classifications are as follows:
1. Balanced proportion of all components of breast tissue with a slight predominance of fibrous tissue
2. Predominance of fat tissue
3. Predominance of fat tissue with retroareolar residual fibrous tissue
4. Predominantly nodular densities
5. Predominantly fibrous tissue (dense breast)

Classes 4 and 5 are considered high risk, meaning that it is difficult to detect cancers in the breast with those patterns, whereas classes 1, 2 and 3 are considered lower risk as it is easier to spot cancerous regions.

Some therapies may alter the pattern by increasing parenchymal density, as in hormone replacement therapy (HRT), or reducing it as in therapies with selective oestrogen-receptor modulators (SERM).

Similarly, breast density categories are classified by radiologists using the BI-RADS system. Again, this classification is used for quality control purposes. For example, it is very difficult to spot an anomaly in dense breasts. There are four categories in the BI-RADS system:
A. The breasts are almost entirely fatty
B. There are scattered areas of fibroglandular density
C. The breasts are heterogeneously dense, which may obscure small masses
D. The breasts are extremely dense, which lowers the sensitivity of mammography Importantly, breast densities and tissue patterns are also known to have a mutual correlation to breast cancer development.

The complexity of assessing the images may cause difficulty when it comes to detecting abnormalities or diseases accurately and precisely, thus affecting the determination of diagnosis and therapeutic preparation. Therefore, meaningful medical image data analysis plays an important role in stages of cancer identification and treatment, as well as in further research.

However, the commonly used method of manual classification may lead to disagreement and classification error, which can prove crucial in medical treatment.

The present invention provides a novel method and system that combines quantitative estimation of density and qualitative estivation of tissue patterns using deep learning to aid the assessment of confounding factors in mammography.

SUMMARY OF THE INVENTION

Aspects and/or embodiments seek to provide a method of automatically classifying the tissue type and breast density of mammograms. Aspects and/or embodiments also seek to address the problems relating to human inaccuracy and highly skilled human resources.

According to a first aspect, there is provided a computer-aided method of analysing mammographic images, the method comprising the steps of: receiving a mammogram; segmenting one or more anatomical regions of the mammogram; identifying a tissue type and a density category classification for an anatomical region; and using the identified tissue type and density category classifications to generate classifications output for the mammogram.

In this way, classification of a mammogram can be automatically performed and thereby reducing human error and need for additional highly skilled medical professionals. It can also improve the analysis of mammographic image with the possibility of jointly estimating the tissue patterns and density category which generates better overall classification results.

The term segmentation does not merely represent dividing an image into one or more parts, for example, by using a bounding box around a particular region or identifying a central location of a particular region. Instead, the segmentation provided by this method determines a number of useful characteristic data, such as area, shape and size, which is more precise than traditional methods. As a result, this segmentation method can be used to more accurate indicate a malignant tumour. In addition, the method disclosed herein is operable to segment a region without any prior input other than an image and requires no feature engineering steps.

Optionally, the step of calibration of intensity levels based on standard anatomical structures is provided. The calibration of intensity levels can more efficiently identify regions of interest in a mammography.

In one embodiment, the step of segmenting one or more anatomical regions comprises determining a primary anatomical region of the mammogram. Optionally the primary anatomical region comprises a region where parenchyma is present. This can be considered to be a region of interest.

Optionally, this embodiment further comprises the steps of selecting one or more sample areas of the primary anatomical region; and identifying the tissue type and the density category classification in dependence upon the sample area.

Selecting a sample area to represent the region of interest can decrease the computational power needed by the system to correctly classify the tissue type and density category. The size of the sample can be varied in accordance with the input parameters of the convolution network.

In another embodiment, the step of segmenting one or more anatomical regions comprises determining a secondary anatomical region of the mammogram. Optionally, the secondary anatomical region comprises a region where parenchyma is not present.

Optionally, in this embodiment, the step of identifying the tissue type and the density category classification is in dependence upon the secondary anatomical region.

Optionally, the step of identifying the tissue type and the density category is performed in one or more convolutional neural networks, CNN. Optionally, the one or more CNN is trained to classify the tissue type and density category. Optionally, the at least one CNN is trained independently to classify tissue type or density category.

In this way, the identification of the tissue type and density category is performed automatically using well trained convolution networks. Convolution networks can be used regardless of whether a parenchyma is detected or not.

Optionally, the step of segmentation is carried out in a fully convolution network, FCN. In this way, the anatomical segmentation is also automatically performed.

Optionally, the classification output for the mammogram comprises a joint tissue type and density category classification. Providing a joint estimate of tissue pattern and density can produce more accurate and discriminative analyses of mammographic images.

Optionally, the step of receiving the mammogram comprises the use of one or more digital imaging and communications in medicine, DICOM, files.

Optionally, the one or more anatomical region comprises the entire breast area.

Optimally, the one or more sample area is selected using uniform or Poisson sampling.

Optionally, the one or more sample area is selected in dependence upon the input of the one or more CNN.

According to a second aspect, there is provided an apparatus to perform the method of any preceding claim.

According to third aspect, there is provided a system operable to perform the method of any preceding claim.

According to a fourth aspect, there is provided a computer program product operable to perform the aforementioned method.

According a fifth aspect, there is a method for training one or more neural networks to classify a mammogram, the method comprises, receiving a mammogram, segmenting one or more anatomical regions of the mammogram, identifying a tissue type and a density category classification for an anatomical region and using the identified tissue type and density category classifications to train the one or more neural networks.

BRIEF DESCRIPTION OF DRAWINGS

Embodiments will now be described, by way of example only and with reference to the accompanying drawings having like-reference numerals, in which.

SPECIFIC DESCRIPTION

Figure 1:
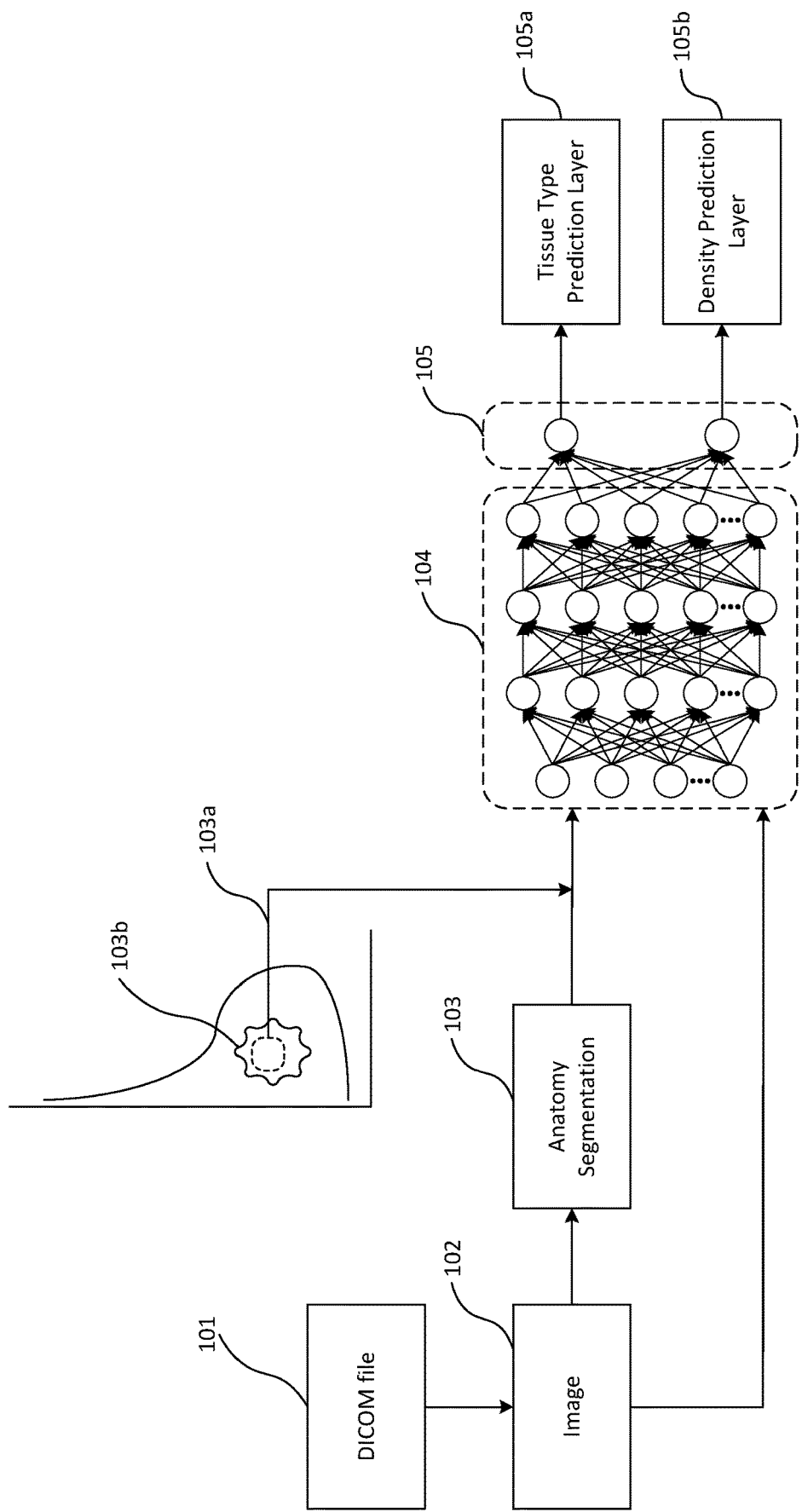
FIG. 1 illustrates a flowchart showing the method of the present invention.

FIG. 1 depicts an example embodiment of the present invention. Where appropriate, the same reference numerals have been used in FIGS. 1a and 2. The invention will now be described using FIGS. 1-2.

As seen in FIG. 1, having performed a medical scan of a patient (mammography), the scanned images are collated in DICOM format 101, which is a file format commonly used to store medical images. The method uses pre-processed data that is stored on a Picture Archiving Communication Systems (PACS) that radiology departments use in hospitals. The output of this method also enriches the PACS database to improve future applications of analysing mammographic images.

As previously mentioned, an important aspect of analysing mammographic images is anatomically segmenting the mammographic images 103, 202.

Figure 2:
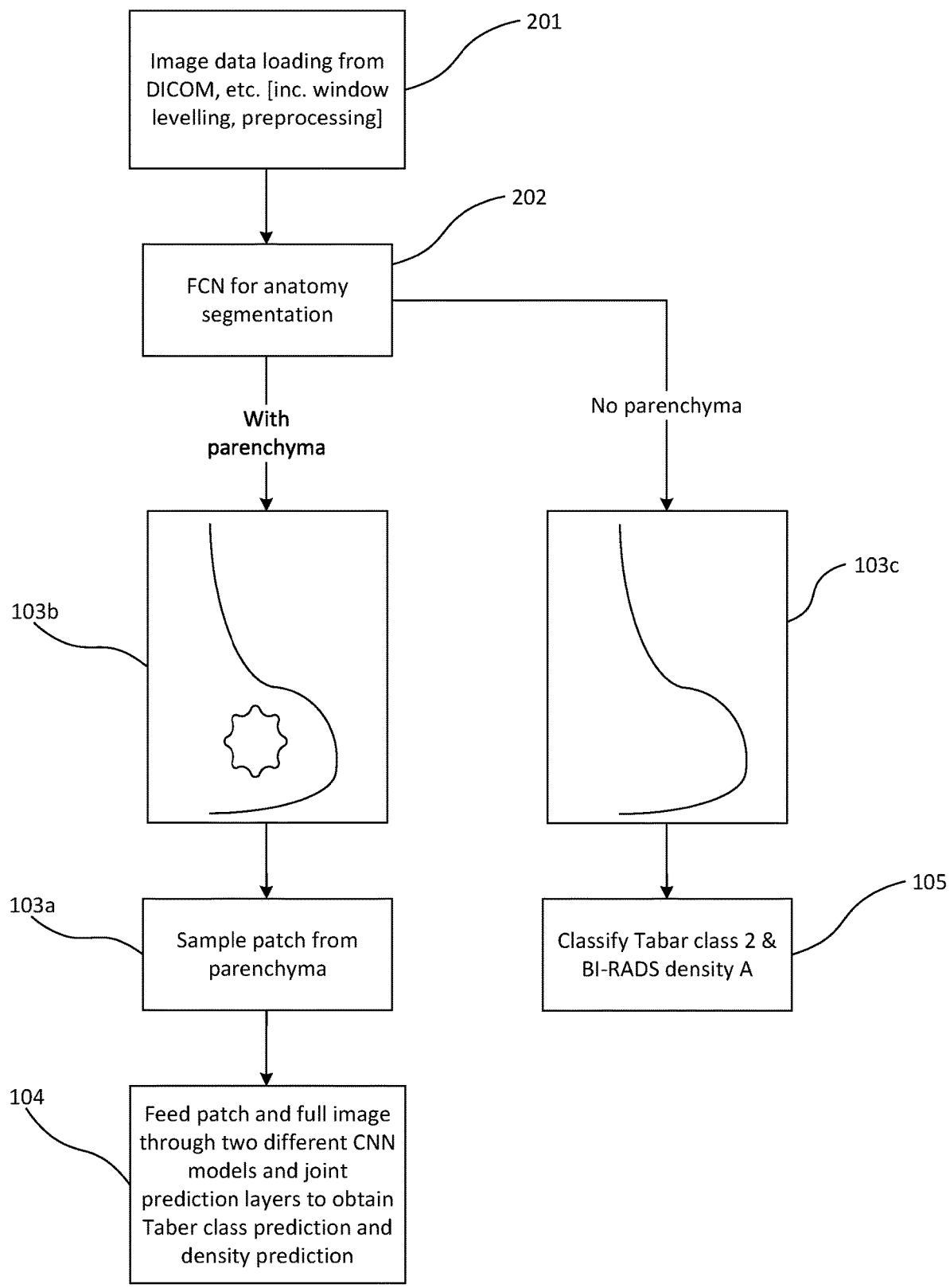
FIG. 2 illustrates a flowchart of how anatomical segmentation is used for the present invention.

As an example, FIG. 2 depicts the use of anatomically segmenting the mammographic images using fully convolution networks, FCN. In this example, the image data is captured from the DICOM file and may require some form of pre-processing before being used by the FCN 201. This may include various techniques such as window levelling, etc.

However, for the purposes of this embodiment, any method of anatomical segmentation can be used.

After the anatomical regions have been segmented, the system identifies whether or not parenchyma is detected in the breast. Parenchyma may also be considered as an anatomical region. As illustrated in FIG. 2, when no parenchyma is detected 103c, the system automatically classifies the breast with tissue type class 2 (Tabar) and a breast density category A (BI-RADS).

On the other hand, if parenchyma is detected 103b then the system follows a different approach. As depicted in FIGS. 1 and 2, when parenchyma is found in the image, a patch is sampled from the parenchyma region 103a. The patch can be sampled using uniform sampling or Poisson sampling, and the size of the patch can be varied.

Once acquired, the sample patch is fed into a convolutional neural network (CNN) 104 which is trained to classify the patch under one of the remaining four tissue types (Tabar) and one of the remaining three density categories (BI-RADS).

Figure 1A:
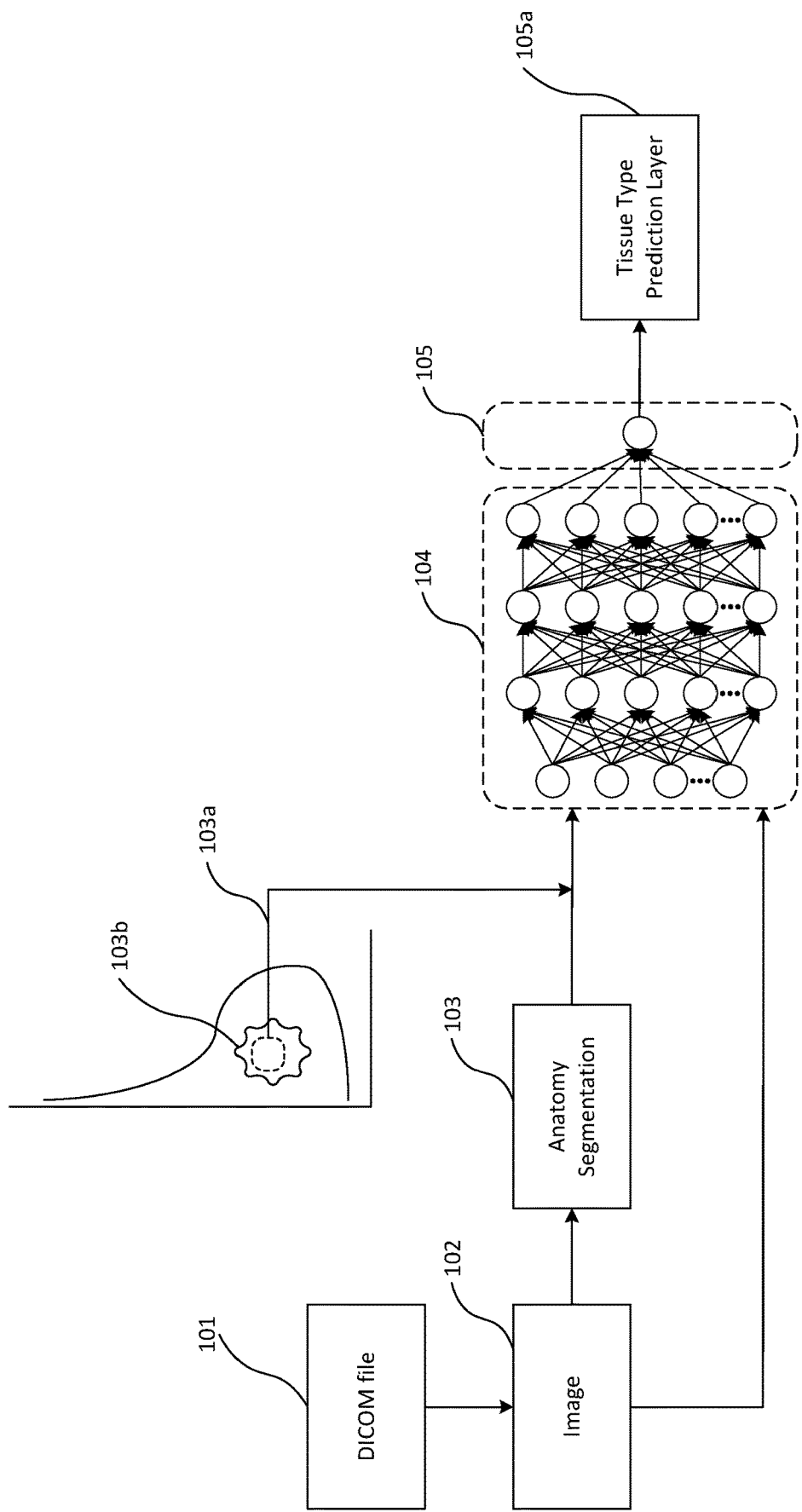
FIG. 1a illustrates a flowchart wherein the convolution networks are trained to predict the tissue type/pattern of the mammogram independently.
Figure 1B:
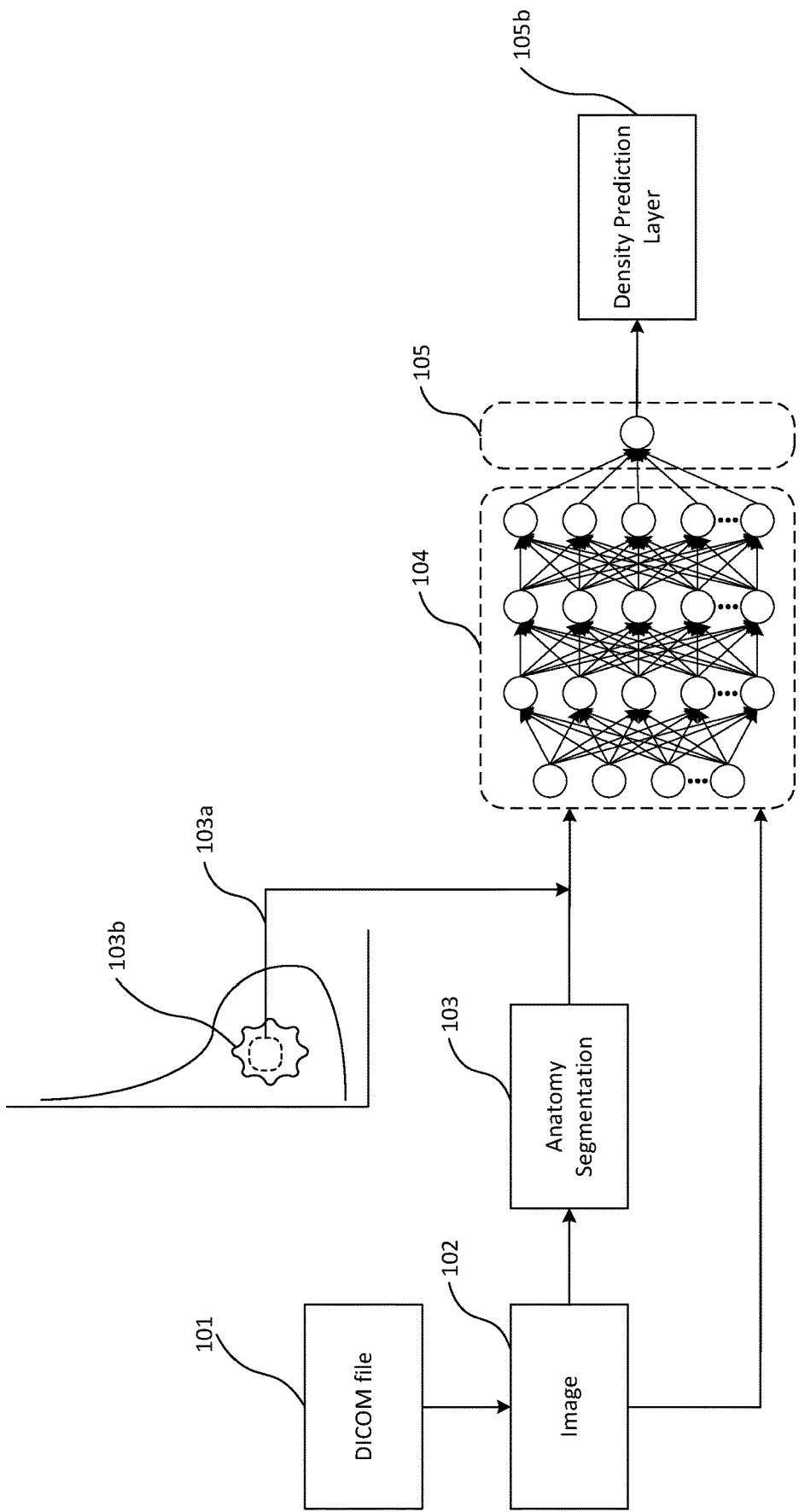
FIG. 1b illustrates a flowchart wherein the convolution networks are trained to predict the density of the mammogram independently.

In some embodiments, each CNN node may have been trained to focus on a specific aspect of breast density or tissue type/pattern, or an ensemble of different CNN nodes and/or models may be used in combination to classify the sample patches and/or mammographic images. As an example, FIG. 1a depicts two CNN models 104a that are independently trained to predict tissue type/pattern and breast density.

This embodiment utilises deep learning techniques to train and develop the convolution network. A large database of full-field digital mammograms can be used to train the system to correctly classify the mammogram.

With the CNN having classified the tissue type and breast density of the sample patch, the CNN can now predict and output the tissue type and density classifications of the full mammographic image 105. As seen in FIG. 1, the full mammographic image 102 is fed into the image pathway of the CNN. In another embodiment, the sample patch and full mammographic image are fed through different CNN models before a joint prediction layer obtains a tissue type and density category classification.

The joint estimation of tissue type and breast density yields a more accurate and discriminative categorisation of mammograms and therefore even lead to better diagnostic planning and improved patient care. The present invention therefore improves the quality control analysis of mammography readings.

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

Any system feature as described herein may also be provided as a method feature, and vice versa. As used herein, means plus function features may be expressed alternatively in terms of their corresponding structure.

Any feature in one aspect of the invention may be applied to other aspects of the invention, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention claimed is:

1. A computer-aided method of analyzing mammographic images, the method comprising:
   receiving a mammographic image;
   segmenting the mammographic image into one or more anatomical regions;
   identifying a Tabar tissue type and a density category classification for at least one of the one or more anatomical regions, wherein identifying the Tabar tissue type and the density category classification is performed in one or more convolutional neural networks (CNN);
   outputting the Tabar tissue type and the density category classification from the one or more CNNs; and
   using the identified Tabar tissue type and density category classification to generate one or more classifications for the mammographic image.

2. The method of claim 1, further comprising calibrating intensity levels based on standard anatomical structures.

3. The method of claim 1, wherein segmenting the mammographic image comprises determining a primary anatomical region of the mammographic image, and/or determining a secondary anatomical region of the mammographic image.

4. The method of claim 3, wherein the primary anatomical region comprises a region where parenchyma is present.

5. The method of claim 3, further comprising:
   selecting one or more sample areas of the primary anatomical region, wherein the identifying comprises identifying the Tabar tissue type and the density category classification for the primary anatomical region in dependence upon the selected one or more sample areas.

6. The method of claim 3, wherein the secondary anatomical region comprises a region where parenchyma is not present.

7. The method of claim 5, wherein both the one or more sample areas and the mammographic image are provided as an input for the one or more CNNs.

8. The method of claim 5, wherein the one or more sample areas is selected using uniform or Poisson sampling.

9. The method of claim 7, wherein the one or more sample areas is selected in dependence upon the input for the one or more CNNs.

10. The method of claim 6, wherein the identifying comprises identifying the Tabar tissue type and the density category classification in dependence upon parenchyma not being present in the secondary anatomical region.

11. The method of claim 1, wherein the one or more CNNs are independently trained to classify the Tabar tissue type or density category classification.

12. The method of claim 1, wherein segmenting the mammographic image is carried out in a fully convolution network (FCN).

13. The method of claim 1, wherein the one or more classifications for the mammographic image comprises a joint Tabar tissue type and density category classification.

14. The method of claim 1, wherein receiving the mammographic image comprises receiving one or more digital imaging and communications in medicine (DICOM) files.

15. The method of claim 1, wherein the one or more anatomical regions comprises an entire breast area.

16. An apparatus operable to perform the method of claim 1.

17. The method of claim 1, wherein segmenting the mammographic image comprises determining area, shape, and/or size of the one or more anatomical regions.

18. A method for training one or more neural networks to classify a mammogram, the method comprises:
   receiving a mammographic image;
   segmenting the mammographic image into one or more anatomical regions;
   identifying a Tabar tissue type and a density category classification for at least one of the one or more anatomical regions; and
   using the identified Tabar tissue type and density category classifications to train the one or more neural networks, such that the trained one or more neural networks are configured to identify a Tabar tissue type and a density category classification in one or more anatomical regions within a received mammographic image, and configured to output the identified Tabar tissue type and the identified density category classification.

19. A computer program product including one or more non-transitory machine readable mediums encoded with instructions that when executed by one or more processors cause a process to be carried out for analyzing mammographic images, the process comprising
   receiving a mammographic image;
   segmenting the mammographic image into one or more anatomical regions;
   identifying a Tabar tissue type and a density category classification for at least one of the one or more anatomical regions, wherein identifying the Tabar tissue type and the density category classification is performed in one or more convolutional neural networks (CNN);
   outputting the Tabar tissue type and the density category classification from the one or more CNNs; and
   using the identified Tabar tissue type and density category classifications to generate one or more classifications for the mammographic image.

20. The computer program product of claim 19, wherein the one or more classifications for the mammographic image comprises a joint Tabar tissue type and density category classification.

* * * * *